US008075915B2

(12) United States Patent
Buchalter

(10) Patent No.: US 8,075,915 B2
(45) Date of Patent: Dec. 13, 2011

(54) COMPOSITION AND METHOD OF TRANSMITTING ULTRASONIC AND ELECTRICAL IMPULSES USING A PHYSIOLOGICALLY COMPATIBLE CONDUCTIVE AGENT

(76) Inventor: Gilbert Buchalter, Millburn, NJ (US)

( * ) Notice: Subject to any disclaimer, the term of this patent is extended or adjusted under 35 U.S.C. 154(b) by 1830 days.

(21) Appl. No.: 11/237,438

(22) Filed: Sep. 28, 2005

(65) Prior Publication Data

US 2007/0071707 A1    Mar. 29, 2007

(51) Int. Cl.
*A61K 9/14* (2006.01)
*H01B 1/00* (2006.01)
*H01B 1/02* (2006.01)
(52) U.S. Cl. ............... 424/484; 252/500; 252/518.1
(58) Field of Classification Search ............ None
See application file for complete search history.

(56) References Cited

U.S. PATENT DOCUMENTS

| | | | | |
|---|---|---|---|---|
| 4,002,221 A | * | 1/1977 | Buchalter | 181/0.5 |
| 4,693,711 A | * | 9/1987 | Bremer et al. | 604/306 |
| 5,954,675 A | * | 9/1999 | Dellagatta | 601/3 |

* cited by examiner

*Primary Examiner* — Brian-Yong Kwon
*Assistant Examiner* — Lyndsey Beckhardt
(74) *Attorney, Agent, or Firm* — Hoffman & Baron, LLP

(57) ABSTRACT

The present invention provides a physiologically compatible conductive agent comprising (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %; (b) an unbranched or branched alcohol having from 1 to about 4 carbon atoms present in an amount up to about 70 wt. %; and (c) the balance water. The present invention also provides a physiologically compatible conductive agent comprising long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %; (b) a surface tension reducing amount of a surfactant; and (c) the balance water. The present invention further provides methods for transmitting electrical or ultrasonic impulses to a surface in contact with a transducer with a conductivity gap by applying to the conductivity gap the novel physiologically compatible conductive agents. The present invention also provides methods for preparing the physiologically compatible conductive agents of the present invention.

14 Claims, No Drawings

COMPOSITION AND METHOD OF TRANSMITTING ULTRASONIC AND ELECTRICAL IMPULSES USING A PHYSIOLOGICALLY COMPATIBLE CONDUCTIVE AGENT

BACKGROUND OF THE INVENTION

1. Field of the Invention

The present invention provides a physiologically compatible conductive agent comprising (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %; (b) an unbranched or branched alcohol having from 1 to about 4 carbon atoms present in an amount up to about 70 wt. %; and (c) the balance water. The present invention also provides a physiologically compatible conductive agent comprising long chain water-soluble ionic polymeric thickening agent selected from the group consisting of a copolymer of methyl vinyl ether and maleic anhydride, carboxy polymethylene polymer, and mixtures thereof, present in an amount from about 0.05 wt % to about 10 wt. %; (b) a surface tension reducing amount of a surfactant; and (c) the balance water. The present invention further provides methods for transmitting electrical or ultrasonic impulses to a surface in contact with a transducer with a conductivity gap by applying to the conductivity gap the novel physiologically compatible conductive agents. The present invention also provides methods for preparing the physiologically compatible conductive agents of the present invention.

2. Description of the Background

The application of electrical and ultrasonic energy in the form of impulses to stimulate or monitor the progress of medical therapy or physical rehabilitation are old and well known techniques. These techniques generally rely upon the use of a transducer applied to a surface, such as electrodes, for applying electrical impulses, or a sound transducer for applying ultrasonic impulses. The surface to which the transducer may be applied may be the skin of an animal or a human or the transducer may be applied to the surface of an article for non-destructive testing purposes.

During the application of electrical impulses to the skin of an animal or person, the amperage which is applied may vary and can produce undesirable differences in the muscular action generated by the electrical current. Since skin has electrical resistance, the currents generated by the electrodes may irritate the skin. Generally, it is necessary to cover the electrode with an adsorbent material or apply a conductive gel to the skin of the animal or human. Conductive gels which are commercially available have the disadvantage of tending to liquefy under the influence of the ingredients in perspiration, such as body salts, and in the veterinary field cannot always penetrate and activate the surface of animal skin because of the oily fur and skin in animals.

U.S. Pat. No. 4,002,221 discloses a method for transmitting electrical impulses to a surface in contact with a transducer with a conductivity gap comprising applying a transducer coupling agent to the conductivity gap.

SUMMARY OF THE INVENTION

The present invention provides a physiologically compatible conductive agent comprising:
(a) long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent;
(b) an unbranched or branched alcohol having from 1 to about 4 carbon atoms present in an amount up to about 70 wt. %; and
(c) the balance water;
wherein the physiologically compatible conductive agent has a pH from about 3.5 to about 11.5.

The present invention also provides a physiologically compatible conductive agent comprising:
(a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent;
(b) a surface tension reducing amount of a surfactant; and
(c) the balance water; wherein the physiologically compatible conductive agent has a pH from about 3.5 to about 11.5.

The present invention further provides a method for transmitting electrical or ultrasonic impulses to a surface in contact with a transducer with a conductivity gap by applying to the conductivity gap a physiologically compatible conductive agent comprising:
(a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent;
(b) an unbranched or branched alcohol having from 1 to about 4 carbon atoms present in an amount up to about 70 wt. %; and
(c) the balance water;
wherein the physiologically compatible conductive agent has a pH from about 3.5 to about 11.5.

The present invention still further provides a method for transmitting electrical or ultrasonic impulses to a surface in contact with a transducer with a conductivity gap by applying to the conductivity gap a physiologically compatible conductive agent comprising:
(a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent;
(b) a surface tension reducing amount of a surfactant; and
(c) the balance water;
wherein the physiologically compatible conductive agent has a pH from about 3.5 to about 11.5.

DETAILED DESCRIPTION OF THE INVENTION

The present invention provides physiologically compatible conductive agents, in the form of gel compositions, containing a primary thickening agent, e.g., a long chain water-soluble ionic polymer, optionally combined with a small but effective amount of an auxiliary hydroxy-containing thickening agent, e.g., a hydroxy alkyl cellulose polymer. The conductive agent is particularly suitable for use with transducers wherein the conductive agent is introduced between the transducer and the skin in contact with a transducer. The physiologically compatible conductive agents of this invention, useful for transmitting electrical or ultrasonic impulses to a surface, exhibit outstanding gelling properties as a result of the particular combination of the thickening agents in the particular proportions. The physiologically compatible conductive agents do not corrode the transducer element and do not substantially leak out from the area of contact. The physiologically compatible conductive agents are particularly useful for transmitting ultrasonic impulses in the veterinary field because the conductive agents contain a low molecular weight alcohol or a surfactant to penetrate the oily fur and skin in animals to activate the surface of animal skin for transmitting ultrasonic impulses.

Applicant's invention provides a physiologically compatible conductive agent comprising (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent; (b) an unbranched or branched alcohol having from 1 to about 4 carbon atoms present in an amount up to about 70 wt. %; and (c) the balance water. The physiologically compatible conductive agent has a pH from about 3.5 to about 11.5.

Applicant's invention also provides a physiologically compatible conductive agent comprising (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent; (b) a surface tension reducing amount of a surfactant; and (c) the balance water. The physiologically compatible conductive agent has a pH from about 3.5 to about 11.5.

Applicant's invention further also provides a method for transmitting electrical or ultrasonic impulses to a surface in contact with a transducer with a conductivity gap by applying to the conductivity gap a physiologically compatible conductive agent comprising (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05wt. % to about 10 wt. %, wherein the thickening agent has a Brookfield Viscosity (CPS) of from about 1,000 to about 1,000,000 at 1 wt. % concentration in water neutralized with an alkaline agent; (b) an unbranched or branched alcohol having from 1 to about 4 carbon atoms present in an amount up to about 70 wt. %; and (c) the balance water. The physiologically compatible conductive agent has a pH from about 3.5 to about 11.5.

Applicant's invention still further also provides a method for transmitting electrical or ultrasonic impulses to a surface in contact with a transducer with a conductivity gap by applying to the conductivity gap a physiologically compatible conductive agent comprising (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent; (b) a surface tension reducing amount of a surfactant; and (c) the balance water. The physiologically compatible conductive agent has a pH from about 3.5 to about 11.5.

The primary thickening agent in (a) is an alkali metal salt of a long chain ionic water-soluble organic polymer. The primary thickening agents are polyelectrolyte polymers that have outstanding gelling properties. Generally, the higher the molecular weight of the primary thickening agent, the more preferred the thickening agent is for the purpose of thickening. Polar groups must also be present in the primary thickening agent in order to allow it to be usable in water gels. The primary thickening agents do not lose water solubility as their molecular weight increases unless they become crosslinked. Examples of such polymeric thickening agents include those selected from the group consisting of copolymers of methyl vinyl ether and maleic acid, carboxy polymethylene polymers, and mixtures thereof. Copolymers of methyl vinyl ether and maleic acid are available under the trademark Gantrez™ and are sold by Kline & Company, Little Falls, N.J. Carboxy polymethylene polymers are cross-linked polyacrylic acid polymers available under the trademark Carbopol™ and are sold by Noveon, Inc. Cleveland, Ohio. Anyone of the Carbopol™ series, such as Carbopol™ 934, Carbopol™ 940, Carbopol™ 941, may be used.

In general, the primary thickening agent component will have a molecular weight (Staudinger) of from about 30,000 to about 2,000,000, preferably from about 60,000 to about 500,000, and more preferably from about 100,000 to 300,000. There is not an established upper limit for the degree of polymerization above which the thickening agents no longer function as efficient thickening agents.

The molecular weights of very high molecular weight polymeric compounds are difficult to determine and the weights obtained will generally vary widely depending upon the method used to determine them. Molecular weights for polymeric materials usually constitute an average of the molecular weights of the molecules present. Methods for measuring the molecular weights of polymeric compounds include osmometric, cryoscopic, ebullioscopic, static and dynamic light scattering, specific viscosity, intrinsic viscosity, and ultra centrifuging techniques.

Viscosity is a property which is much more frequently used than molecular weights to characterize polymeric compounds due to the comparatively less complicated methods for obtaining viscosity data. There is a direct correlation between the viscosity of polymeric compounds and their relative molecular weights and since such figures can frequently be more available than molecular weights, the polymeric thickening agents described in this invention may be characterized in terms of viscosity. Thus, the viscosities of the primary thickening agents which can be used in the invention have a Brookfield Viscosity (CPS-centipoises per second) (20 rpm, spindle #5) of from about 1,000 to about 1,000,000, preferably from about 15,000 to about 90,000, and most preferably from about 18,000 to 80,000 at 1 wt. % aqueous concentration. These viscosities are given in terms of polymeric thickening agents which have been neutralized to a pH of about 7.

Alkaline agents, such as alkali metal hydroxides and certain organic amines may be used to neutralize the primary thickening component of the inventive composition. Sodium and potassium hydroxides are preferred and sodium hydroxide is particularly preferred because it imparts improved ultrasound conductivity to the resultant gel compositions.

Generally, the primary thickening agent is present in the physiologically compatible conductive agent in an amount from about 0.05 wt. % to about 10 wt. %, preferably from about 0.25 wt. % to about 5 wt. %, and most preferably from about 0.8 wt. % to about 3.5 wt. %.

In one embodiment, the agent in (b) employed to penetrate and activate the oily fur and skin in animals is an unbranched or branched alcohol having from 1 to about 4 carbon atoms. The unbranched or branched alcohol may be selected from the group consisting of methanol, ethanol, n-propanol, i-propanol, n-butanol, sec-butanol, and tert-butanol. Preferably, the unbranched or branched alcohol may be selected from the group consisting of ethanol, n-propanol, i-propanol, and n-butanol. More preferably, the unbranched or branched alcohol is n-propanol or i-propanol. Most preferably, the unbranched or branched alcohol may is i-propanol. The presence of the unbranched or branched alcohol serves to penetrate the oily fur and skin in animals so as to allow the physiologically compatible conductive agent to penetrate and activate the surface of animal skin. The unbranched or branched alcohol may be present in the physiologically compatible conductive agent in an amount up to about 70 wt. %; preferably from about 10% wt. to about 40% wt., more preferably from about 15% wt. to about 30% wt., and most preferably from about 15% wt. to about 25% wt.

In another embodiment, the agent in (b) employed to penetrate and activate the oily fur and skin in animals is a surfactant. Surfactants are surface active agents that reduce surface tension when dissolved in water solutions, or which reduce interfacial tension between two liquids, or between a liquid and a solid. Generally, water-soluble surfactants contain a hydrophobic portion, usually a long chain hydrocarbon, attached to a hydrophilic/water-soluble functional group. A surfactant can be classified by the presence or absence of formally charged groups. A nonionic surfactant has no charge groups. An ionic surfactant carries a net charge. If the charge is negative, the surfactant is termed anionic. If the charge is positive, it is termed cationic. If a surfactant contains two oppositely charged groups, it is termed ampholytic. Some commonly encountered nonionic surfactants include alkyl poly(ethyleneoxide) and alkyl polyglucosides, including octyl glucoside and decyl maltoside. Some commonly encountered anionic surfactants include soaps, or fatty acid salts, sodium dodecyl sulfate (SDS), and other alkyl sulfate salts. Some commonly encountered cationic surfactants include cetyl trimethylammonium bromide (CTAB), and other alkyltrimethylammonium salts, cetyl pyridinium chloride, and polyethoxylated tallow amine (POEA). Some commonly encountered ampholytic surfactants include dodecyl betaine and dodecyl dimethylamine oxide. Other useful surfactants may be selected from the group consisting of sodium dodecylsulfate, sodium cholate, sodium deoxycholate, N-lauroylsarcosine sodium salt, lauryldimethylamine-oxide, cetyltrimethylammonium bromide, and bis(2-ethylhexyl)sulfosuccinate sodium salt.

The amount of surfactant present in the physiologically-compatible conductive agent of the present invention is a surface tension reducing amount. A surface tension reducing amount is that amount of surfactant necessary to penetrate the oily fur and skin in animals so as to allow the physiologically compatible conductive agent to penetrate and activate the surface of animal skin. The exact amount of surfactant that is effective is a matter of preference that is determined by such factors as the type of surfactant being employed as well as the other ingredients incorporated in the physiologically compatible conductive agent. In a preferred embodiment, the surfactant may be present in the physiologically compatible conductive agent in an amount up to about 10 wt. %, preferably from about 0.1% wt. to about 8% wt., more preferably from about 0.5% wt. to about 6% wt., and most preferably from about 1% wt. to about 5% wt.

Water in (c) is added to make up the balance of the physiologically compatible conductive agent composition.

The pH of the gel will range from about 3.5 to about 11.5, preferably from about 5 to about 9.5, and most preferably from about 6 to about 7.5. In general, the pH of the physiologically compatible conductive agent will be adjusted to be as close to the pH of the human skin as possible.

Optionally, an auxiliary thickening agent may be employed which is a non-ionic marginally water-soluble polymer with a long chain cellulosic backbone having at least one primary hydroxy group attached to each repeating cellulose molecule. The mono-, bi-, and tri-valent salts are progressively undesirable factors in perspiration in that they are known to cause degradation of electrode gels. This results in a liquification which causes conventional gels to thin out and become ineffective. The use of the auxiliary thickening agents in the present invention is effective in preventing this liquification.

Preferably, the auxiliary thickening agent has the highest molecular weight possible without being completely insoluble in a thickened water-alcohol mixture. Examples of such auxiliary thickening agents are hydroxy methyl cellulose, hydroxy ethyl cellulose, and hydroxy propyl cellulose, and the like, and mixtures thereof. The length of the alkyl group in the long chain cellulosic backbone usually ranges from 1 to about 10 carbon atoms, preferably from 1 to about 7 carbon atoms, and most preferably from 1 to about 5 carbon atoms. Preferably, the auxiliary thickening agent used has no metallic cation constituent. The particularly preferred auxiliary thickening agent is hydroxy ethyl cellulose (HEC) available under the trade name Cellosize™ and sold by the Dow Chemical Company.

In general, the auxiliary thickening agent has a Brookfield Viscosity (CPS-centipoises per second) (20 rpm) of from about 100 to about 10,000, preferably from about 250 to about 5,000, and most preferably from about 1,000 to about 4,000.

Generally, the auxiliary thickening agent is present in the physiologically compatible conductive agent in an amount from about 0.001 wt. % to about 3 wt. %, preferably from about 0.01 wt. % to about 2 wt. %, and most preferably from about 0.05 wt. % to about 1 wt. %.

Optionally, a polyalkylene glycol humectant may be employed which is an alkylene group containing from about 2 to about 10 carbon atoms, preferably from 2 to 5 carbon atoms, and most preferably is propylene glycol. The polyalkylene glycol humectant is present in the physiologically compatible conductive agent in an amount from about 10 wt. % to about 25 wt. %, preferably from about 14 wt. % to 20 wt. %, and most preferably from about 16 wt. % to about 18.5 wt. % The polyalkylene glycol humectant slows drying time, permits the elimination of auxiliary preservatives, and serves as a wetting or solubilizing agent to lower the total electrical resistance because of its ability to penetrate the innerface.

Optionally, an alkali metal salt of a weak organic acid may be employed which is an alkali metal citrate present in an amount up to about 5 wt. %, and preferably from about 0.8 wt. % to about 3 wt. % of the composition.

The weak organic acid in (e) may be citric acid or other buffering acids such as benzoic acid, salicylic acid, tartaric acid, malic acid, lactic acid, and the like. The weak organic acid may be present in an amount up to about 5 wt. %.

Generally, the preparation of the physiologically compatible conductive agent involves the dispersion of the primary thickening agent component, the auxiliary thickening agent component, the unbranched or branched alcohol and/or surfactant, and the additional ingredients in about half the total water which is needed. The ingredients are then dispersed with high speed mixing using a mixer such as the Lightning line of mixers obtainable from the Mixing Equipment Corp. Subsequently, the balance of the water is added less any water which is needed for the neutralizing agent. The mixture is then allowed to stabilize and an alkaline solution is added to the mixture slowly. The pH is adjusted as described above.

The especially preferred physiologically compatible conductive agents/gels of the present invention comprises a combination of carboxy polymethylene polymer, as the primary thickening agent, and hydroxy ethyl cellulose, as the auxiliary thickening agent, in combination with a water-i-propanol mixture. A particularly preferred composition is one containing sodium. Where very high concentrations of alkali metal ions are desired for exceptional conductivity, about 3 wt. % Carbopol is used supplemented with potassium citrate or sodium citrate and with citric acid as a buffer.

No inorganic salts are added to the physiologically compatible conductive agent/gel composition. In many conventional gels, an inorganic salt is present to provide electrical conduction. Salt is the primary cause of skin irritation. The gel of the invention has a low polarization potential. Indeed, in actual use, it appears to be essentially non-polarizing.

The preferred product of the invention having a careful balance of primary thickening agent, auxiliary thickening agent, humectant, and unbranched or branched alcohol has a unique penetrating action which gives it a total lower electrical resistance between the skin, the gel and the electrode as compared to competitive products.

While the composition and method described constitute preferred embodiments of this invention, it is to be understood that the invention is not limited to this precise form of method and that changes may be made therein without departing from the scope of the invention which is defined in the appended claims.

EXAMPLE 1

A composition of the prior art and a preferred composition of the present invention having the following formulations were prepared for comparison purposes. (All percentages are weight percents unless otherwise indicated).

|  | Most Related Commercial Material | Composition of The Present Invention |
|---|---|---|
| Carboxy Polymethylene (Carbopol 934)[1] | 0.6% | 1–3% |
| Hydroxy Ethyl Cellulose (QP 100M)[2] | — | 0.125–1.5% |
| Isopropyl Alcohol | — | 18–20% |
| Methyl Paraben | 0.18% | 0.18% |
| Propyl Paraben | 0.03% | 0.03% |
| Perfume | 0.004% | — |
| F.D. & C. Color | 0.001% | 0.001% |
| Sodium Hydroxide | 39% (Based on Carbopol) | 39% |
| Potassium Hydroxide | 40% | 35% |
| Water Balance to 100% | | |

[1]Carbopol 934 is a white powder which has a Brookfield RVF or RVJ 20 rpm No.spindle at 25° C. +− 0.5° C. for an 0.2% neutralized solution of from 2,050 to 5,450.
[2]QP 100M (Quick Processing) is a non-ionic water-soluble cellulose ether with a Brookfield Viscosity at 25° C. with Spindle No. 4 at 1 wt. % in $H_2O$ of 2,500 to 3,000 CPS.

The above described commercial material was prepared as follows. The preservatives (methyl and propyl paraben) were dissolved in the isopropyl alcohol. The perfume was then dispersed. One half of the total volume of the water was then added. Carbopol 934 was dispersed with high speed mixing. The dye was then added. The balance of the water was added, less the water needed for dissolving the alkali metal hydroxide.

The composition of the invention was similarly formulated except that citric acid and potassium citrate were preferably added prior to the addition of Carbopol 934 and the hydroxy ethyl cellulose was preferably added either simultaneously with the Carbopol 934 or after the Carbopol 934.

Both mixtures were allowed to stand without further agitation for several days to allow the air bubbles to disperse. Upon completion of this stabilizing time, the alkali metal hydroxide was dissolved in the proper amount of water and added to the above mixture with slow agitation until the gel was formed and was mixed until completely uniform.

The mixture prior to neutralization with alkali metal hydroxide was a thin, pourable, milky liquid with the viscosity of light cream. The mixture after neutralization was a clear, sparkling gel with a viscosity similar to that of mayonnaise or sour cream.

The major differences in the formulation of the gel composition of the invention in contrast to the prior art gel are that the methyl and propyl paraben could be eliminated since the presence of unbranched or branched alcohol was sufficient for preservation. However, with lower amounts of unbranched or branched alcohol, these preservatives may be used.

The hydroxy ethyl cellulose (HEC) was dispersed simultaneously with the Carbopol 934. This resulted in a thicker or higher viscosity pre-neutralized liquid since the thickening ability of HEC is not dependent upon pH.

Neutralization was effected with sodium or potassium hydroxide as the alkaline agent, preferably sodium hydroxide which is a better ultrasound conductor.

The elimination of the methyl paraben as a preservative enabled the production of an odorless product which did not require the necessity of perfume to mask the preservative odor. The optional propylene glycol content of the novel gel composition is higher than that of the prior art gel because in the novel gel composition, it is used for three different and distinct purposes. In the prior art gel, it is used solely as a humectant for retarding drying time. This higher concentration enables it to be used as a preservative in the composition. It also has the advantage of being a wetting or solubilizing agent due to the fact that it is an alcohol.

This wetting, solubilizing and penetrating effect is responsible for lowering the total ultrasound barrier when in use, as it tends to wet, solubility and penetrate the oil-skin barrier.

Another example of a composition for particular use as an ultrasonic gel is one containing approximately ½ of 1 wt. % carboxy polymethylene polymer, approximately ¼ of 1 wt. % hydroxy ethyl cellulose, approximately 18 wt. % of unbranched or branched alcohol having from 1 to about 4 carbon atoms and an amount of sodium hydroxide calculated at 40% of the amount of carboxy polymethylene polymer present. Where the composition is used for transmitting electrical impulses, it is preferred that potassium hydroxide be used in place of sodium hydroxide in an amount 55% by weight of the carboxy polymethylene polymer present.

A preferred gel composition for transmitting electrical impulses is one containing approximately 3 wt. % carboxy polymethylene polymer, approximately ⅛ of 1 wt. % hydroxy ethyl cellulose, approximately 18% isopropyl alcohol, approximately 2.5 wt. % potassium hydroxide based on the total composition, approximately 3 wt. % potassium citrate and approximately 1 wt. % citric acid.

EXAMPLE 2

Tests were performed which show that using the novel gel composition for regular electrocardiogram monitoring allows the use of either a pediatric electrode, or a specially modified electrode (original tests were done using a penny and a lightweight shielded cable instead of the cumbersome and costly suction cup chest electrodes and the strap electrodes for the arm or leg).

The high viscosity of the novel gel composition held the small electrode (pediatric or penny) in place without the necessity of mechanical assistance from the suction cup or straps resulting in a saving time and cost.

EXAMPLE 3

The basic technique for stimulation of denervated muscles with direct current was used. The dispersive pad electrode was thoroughly saturated with warm water and placed outside the area being treated. In all cases, the hand on the affected side was used to complete the circuit.

The felt and asbestos covering was removed from a conventional "diagnostic" tap key electrode. The stainless steel electrode plate used was 2 cm. in diameter. The dispersive electrode was left intact with its commercial covering over the plate. A single sheet of paper toweling cut to size was used over the dispersive pad as a sanitary measure.

The electrode gel composition of the invention described in Example 1 was applied to the active electrode and to the motor point areas with a 0.5 cm. thick glob. A direct current was used for stimulation, interrupted by means of a make and break technique with the tap key electrode. Care was taken to apply minimal pressure on the tap key electrode. Too much pressure on the electrode caused a mechanical removal of the gel, resulting in patient discomfort and diminished response.

Following completion of the treatment, the gel was removed from the skin with a tissue. The active electrode was rinsed under hot water and placed in a cold sterilization pan.

The viscosity of the gel provided constant contact even over hairy areas and structural contours which are usually problem areas. This continuous rather than interrupted contact of the electrode provided a new level of patient comfort. Patient comfort level was also improved through the reduction of intensity and local sensation of heat. The cool skin sensation experienced by the patient diminishes his anxiety regarding burn.

Throughout this disclosure, applicant will suggest various theories or mechanisms by which applicant believes the components in the physiologically compatible conductive agent function in an unexpected manner. While applicant may offer various mechanisms to explain the present invention, applicant does not wish to be bound by theory. These theories are suggested to better understand the present invention but are not intended to limit the effective scope of the claims.

The apparatus useful in accordance with the present invention comprises apparatus well known in the manufacturing arts, and therefore the selection of the specific apparatus will be apparent to the artisan.

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

I claim:

1. A physiologically compatible conductive agent for veterinary use consisting essentially of:
   (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent;
   (b) an unbranched or branched alcohol having from 1 to about 4 carbon atoms present in an amount up to about 70 wt. %; and
   (c) the balance water;
wherein the physiologically compatible conductive agent has a pH from about 3.5 to about 11.5.

2. The conductive agent according to claim 1, wherein the long chain water-soluble ionic polymeric thickening agent is a carboxy polymethylene polymer present in an amount from about 0.25 wt. % to about 5 wt. %, substantially neutralized with sodium or potassium hydroxide.

3. The conductive agent according to claim 1, wherein the alcohol is i-propanol present in an amount from about 10 wt. % to about 40 wt. %.

4. The conductive agent according to claim 1, further comprising a hydroxy alkyl cellulose polymer present in an amount from about 0.001 wt. % to about 3 wt. %.

5. The conductive agent according to claim 1, further comprising a polyalkylene glycol humectant, wherein the alkylene group contains from about 2 to about 10 carbon atoms, present in an amount from about 10 wt. % to about 25 wt. %.

6. The conductive agent according to claim 1, further comprising an alkali metal salt of a weak organic acid present in an amount up to about 5 wt. %.

7. The conductive agent according to claim 1, further comprising a weak organic acid present in an amount up to about 5 wt. %.

8. A method for transmitting electrical or ultrasonic impulses in veterinary practice to a surface in contact with a transducer with a conductivity gap by applying to the conductivity gap a physiologically compatible conductive agent consisting essentially of:
   (a) a long chain water-soluble ionic polymeric thickening agent selected from the group consisting of a copolymer of methyl vinyl ether and maleic anhydride, carboxy polymethylene polymer, and mixtures thereof, present in an amount from about 0.05 wt. % to about 10 wt. %, wherein the thickening agent has a Brookfield Viscosity (CPS) of from about 1,000 to about 1,000,000 at 1 wt. % concentration in water neutralized with an alkaline agent;
   (b) an unbranched or branched alcohol having from 1 to about 4 carbon atoms present in an amount up to about 70 wt. %; and
   (c) the balance water;
wherein the physiologically compatible conductive agent has a pH from about 3.5 to about 11.5; and the unbranched or branched alcohols penetrate to the skin surface in animals to activate the surface for the transmission of ultrasonic impulses.

9. The method according to claim 8, wherein the long chain water-soluble ionic polymeric thickening agent is a carboxy polymethylene polymer present in an amount from about 0.25 wt. % to about 5 wt. %, substantially neutralized with sodium or potassium hydroxide 10. The method according to claim 8, wherein the alcohol is i-propanol present in an amount from about 10 wt. % to about 40 wt. %.

11. The method according to claim 8, further comprising a hydroxy alkyl cellulose polymer present in an amount from about 0.001 wt. % to about 3 wt. %.

12. The method according to claim 8, further comprising a polyalkylene glycol humectant, wherein the alkylene group contains from about 2 to about 10 carbon atoms, present in an amount from about 10 wt. % to about 25 wt. %.

13. The method according to claim 8, further comprising an alkali metal salt of a weak organic acid present in an amount up to about 5 wt. %.

14. The method according to claim 8, further comprising a weak organic acid present in an amount up to about 5 wt. %.

* * * * *